(12) United States Patent
Ahmed et al.

(10) Patent No.: US 10,775,476 B2
(45) Date of Patent: Sep. 15, 2020

(54) DIRECT CLOSED-FORM COVARIANCE MATRIX AND FINITE ALPHABET CONSTANT-ENVELOPE WAVEFORMS FOR PLANAR ARRAY BEAMPATTERNS

(71) Applicant: KING ABDULLAH UNIVERSITY OF SCIENCE AND TECHNOLOGY, Thuwal (SA)

(72) Inventors: Sajid Ahmed, Thuwal (SA); Taha Bouchoucha, Thuwal (SA); Tareq Al-Naffouri, Thuwal (SA); Mohamed-Slim Alouini, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 466 days.

(21) Appl. No.: 15/556,656

(22) PCT Filed: May 17, 2016

(86) PCT No.: PCT/IB2016/052870
§ 371 (c)(1),
(2) Date: Sep. 8, 2017

(87) PCT Pub. No.: WO2016/185384
PCT Pub. Date: Nov. 24, 2016

(65) Prior Publication Data
US 2018/0052219 A1 Feb. 22, 2018

Related U.S. Application Data

(60) Provisional application No. 62/162,909, filed on May 18, 2015.

(51) Int. Cl.
*G01S 7/02* (2006.01)
*G01S 13/87* (2006.01)
*G01S 13/89* (2006.01)

(52) U.S. Cl.
CPC .............. *G01S 7/02* (2013.01); *G01S 13/878* (2013.01); *G01S 13/89* (2013.01)

(58) Field of Classification Search
None
See application file for complete search history.

(56) References Cited

U.S. PATENT DOCUMENTS

2007/0132631 A1 6/2007 Henson et al.
2007/0285336 A1* 12/2007 Kamgaing ........... H01Q 1/2258
343/895

(Continued)

FOREIGN PATENT DOCUMENTS

EP  3021132 A1  5/2016
WO  2010116153 A1  10/2010

OTHER PUBLICATIONS

Ahmed: Ahmed, et al, IEEE transactions on signal processing, vol. 59, No. 11, Nov. 2011 (Year: 2011).*

(Continued)

*Primary Examiner* — Erin F Heard
*Assistant Examiner* — Donald H B Braswell
(74) *Attorney, Agent, or Firm* — Patent Portfolio Builders PLLC

(57) ABSTRACT

Various examples of methods and systems are provided for direct closed-form finite alphabet constant-envelope waveforms for planar array beampatterns. In one example, a method includes defining a waveform covariance matrix based at least in part upon a two-dimensional fast Fourier transform (2D-FFT) analysis of a frequency domain matrix $H_f$ associated with a planar array of antennas. Symbols can be encoded based upon the waveform covariance matrix and the encoded symbols can be transmitted via the planar array of antennas. In another embodiment, a system comprises an N×M planar array of antennas and transmission circuitry configured to transmit symbols via a two-dimensional wave- (Continued)

form beampattern defined based at least in part upon a 2D-FFT analysis of a frequency domain matrix $H_f$ associated with the planar array of antennas.

18 Claims, 7 Drawing Sheets

(56) References Cited

U.S. PATENT DOCUMENTS

| | | | | |
|---|---|---|---|---|
| 2014/0241314 | A1* | 8/2014 | Raleigh | H04B 7/0615 370/330 |
| 2014/0347211 | A1 | 11/2014 | Schoor et al. | |
| 2014/0376656 | A1* | 12/2014 | Agee | H04B 7/0413 375/267 |
| 2017/0279511 | A1* | 9/2017 | Eriksson | H04L 5/0053 |

OTHER PUBLICATIONS

Ahmed, S. et al., "Finite Alphabet Constant-Envelope Waveform Design for MIMO Radar," IEEE Transactions on Signal Processing, Nov. 2011, vol. 59, No. 11, pp. 5326-5337.
Ahmed, S. et al., "Unconstrained Synthesis of Covariance Matrix for MIMO Radar Transmit Beampattern," IEEE Transactions on Signal Processing, Aug. 2011, vol. 59, No. 8, pp. 3837-3849.
Fishler, E_, et al., "MIMO Radar: An Idea Whose Time Has Come," Proceedings of the IEEE Radar Conference, Apr. 2004, pp. 71-78.
Fishler, E., et al., "Spatial Diversity in Radars-Models and Detection Performance," Draft, Apr. 26, 2004, Submitted to the IEEE Transactions on Signal Processing.
Guerci, J.R. "Chapter 3: Optimal and Adaptive MIMO Waveform Design," Principles of Modern Radar: Advanced Applications, Eds. W.L. Melvin and J. A. Scheer, 2013, SciTech.
Hassanien A., et al., "Phased-MIMO Radar: A Tradeoff Between Phased-Array and MIMO Radars," Submitted to the IEEE Transactions on Signal Processing in Jul. 2009, Cornell University Library, (arXiv.org, Aug. 15, 2009).
International Search Report in related International Application No. PCT/IB2016/052870, dated Aug. 8, 2016.
Jardak, S., "Colocated MIMO Radar: Transmit Beamforming, Waveform Design, and Target Parameter Estimation," Thesis, Apr. 2014.
Lipor, J. et al., "Fourier-Based Transmit Beampattern Design Using MIMO Radar," IEEE Transactions on Signal Processing, Draft, Feb. 14, 2014.
Stoica, P. et al., "On Probing Signal Design for MIMO Radar," IEEE Transactions on Signal Processing, Submitted in Mar. 2006.
Stoica, P. et al., "Waveform Synthesis for Diversity-Based Transmit Beampattern Design," IEEE/SP 14th Workshop on Statistical Signal Processing, Aug. 2007, pp. 473-477.
Written Opinion of the International Searching Authority in related International Application No. PCT/IB2016/052870, dated Aug. 8, 2016.
First Examination Report in corresponding/related GC Application No. 2016-31343, dated Feb. 20, 2019 (Documents D1 and D2 were cited in the IDS filed Sep. 8, 2017).
Second Examination Report in corresponding/related GC Application No. 2016-31343, dated Jul. 28, 2019 (Document D1 was cited in the IDS filed Sep. 8, 2017).
Communication Pursuant to Article 94(3) EPC in corresponding/related European Patent Application No. 16725239.4, dated Apr. 29, 2019 (References D1-D4 were cited in the IDS filed Sep. 8, 2017).
Aittomäki, T., et al., "Low-Complexity Method for Transmit Beamforming in MIMO Radars," IEEE International conference on Acoustics, Speech and Signal Processing, Apr. 2007, vol. 2, pp. II-305-II-308.
Aittomäki, T., et al., "Signal Covariance Matrix Optimization for Transmit Beamforming in MIMO Radars," Conference Record of the Forty-First Asilomar Conference on Signals, Systems and Computers, Nov. 2007, pp. 182-186.
Fuhrmann, D.R., et al., "Constant-Modulus Partially Correlated Signal Design for Uniform Linear and Rectangular MIMO Radar Arrays," International Waveform Diversity and Design Conference, Feb. 2009, pp. 197-201.
Fuhrmann, D.R., et al., "Signaling Strategies for the Hybrid MIMO Phased-Array Radar," IEEE Journal of Selected Topics in Signal Processing, Feb. 2010, vol. 4, No. 1, pp. 66-78.
Fuhrmann, D.R., et al., "Transmit Beamforming for MIMO Radar Systems Using Partial Signal Correlation," Conference Record of the Thirty-Eighth Asilomar Conference on Signals, Systems and Computers, Nov. 2004, vol. 1, pp. 295-299.
Fuhrmann, D.R., et al., "Transmit Beamforming for MIMO Radar Systems using Signal Cross-Correlation," IEEE Transactions on Aerospace and Electronic Systems, Jan. 2008, vol. 144, No. 1, pp. 171-186.
Haimovich, A.M., et al., "MIMO Radar with Widely Separated Antennas," IEEE Signal Processing Magazine, Jan. 2008, pp. 116-129.
Li, J., et al., "MIMO Radar with Colocated Antennas," IEEE Signal Processing Magazine, Sep. 2007, pp. 106-114.
Wang, W.-Q., "MIMO SAR Chirp Modulation Diversity Waveform Design," IEEE Geoscience and Remote Sensing Letters, Sep. 2014, vol. 11, No. 9, pp. 1644-1648.
Xu, L., et al., "Target Detection and Parameter Estimation for MIMO Radar Systems," IEEE Transactions on Aerospace and Electronic Systems, Jul. 2008, vol. 44, No. 3, pp. 927-939.

* cited by examiner

DIRECT CLOSED-FORM COVARIANCE MATRIX AND FINITE ALPHABET CONSTANT-ENVELOPE WAVEFORMS FOR PLANAR ARRAY BEAMPATTERNS

CROSS REFERENCE TO RELATED APPLICATIONS

This application claims priority to, and the benefit of, U.S. provisional application entitled "DIRECT CLOSED-FORM COVARIANCE MATRIX AND FINITE ALPHABET CONSTANT-ENVELOPE WAVEFORMS FOR PLANAR ARRAY BEAMPATTERNS" having Ser. No. 62/162,909, filed May 18, 2015, which is hereby incorporated by reference in its entirety.

BACKGROUND

Collocated multiple-input multiple-output (MIMO) radar has a number of advantages over the classical phased-array radars. For example, MIMO radar can yield significant improvement in parameter identifiability, allow for detection of a higher number of targets, and provide enhanced flexibility for transmit beampatterns. In general, imaging radars focus transmitted power in a region-of-interest (ROI) on the ground, which may be defined by a transmit waveform. However, due to the power transmitted in side-lobes, the imaging radar may receive reflected signals from outside the ROI.

SUMMARY

Embodiments of the present disclosure are related to direct closed-form finite alphabet constant-envelope waveforms for planar array beampatterns.

In one embodiment, among others, a method comprises defining a waveform covariance matrix based at least in part upon a two-dimensional fast Fourier transform (2D-FFT) analysis of a frequency domain matrix $H_f$ associated with a planar array of antennas; encoding symbols based upon the waveform covariance matrix; and transmitting the encoded symbols via the planar array of antennas. In another embodiment, a system comprises an N×M planar array of antennas, with N>2 and M>2; and transmission circuitry configured to transmit symbols via a two-dimensional (2D) waveform beampattern defined based at least in part upon a 2D fast Fourier transform (2D-FFT) analysis of a frequency domain matrix $H_f$ associated with the planar array of antennas. In one or more aspects of these embodiments, the transmission circuitry can comprise a processing unit configured to synthesize coded symbols based at least in part upon the 2D waveform beampattern. The transmission circuitry can comprise a memory unit configured to store a plurality of digital bit streams corresponding to the coded symbols; and a front end unit configured to transmit the plurality of digital bit streams corresponding to the coded symbols through the planar array of antennas. The front end unit can be a radar front end unit configured to transmit the coded symbols through a planar array of radar antennas.

In one or more aspects of these embodiments, the frequency domain matrix $H_f$ can be based at least in part upon a defined region of interest (ROI) associated with the planar array of antennas. Individual elements of the frequency domain matrix $H_f$ can correspond to individual antennas of the planar array of antennas. The individual elements corresponding to individual antennas within the ROI are assigned a value of one and the individual elements corresponding to individual antennas outside the ROI can be assigned a value of zero. Individual elements of the waveform covariance matrix can be determined based upon a time domain matrix $H_t$ generated by a two-dimensional inverse discrete Fourier transform (2D-IDFT) of the frequency domain matrix $H_f$. The individual elements R of the waveform covariance matrix can be determined from elements $H_t$ of the time domain matrix $H_t$ based upon $$R(i_1, i_2) = \frac{1}{MN} H_t(\langle i_1 - i_2 \rangle_M, \lfloor i_1 \rfloor_M - \lfloor i_2 \rfloor_M),$$

where $i_1, i_2 = 0, 1, \ldots, MN-1$. The waveform covariance matrix can be a block Toeplitz.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
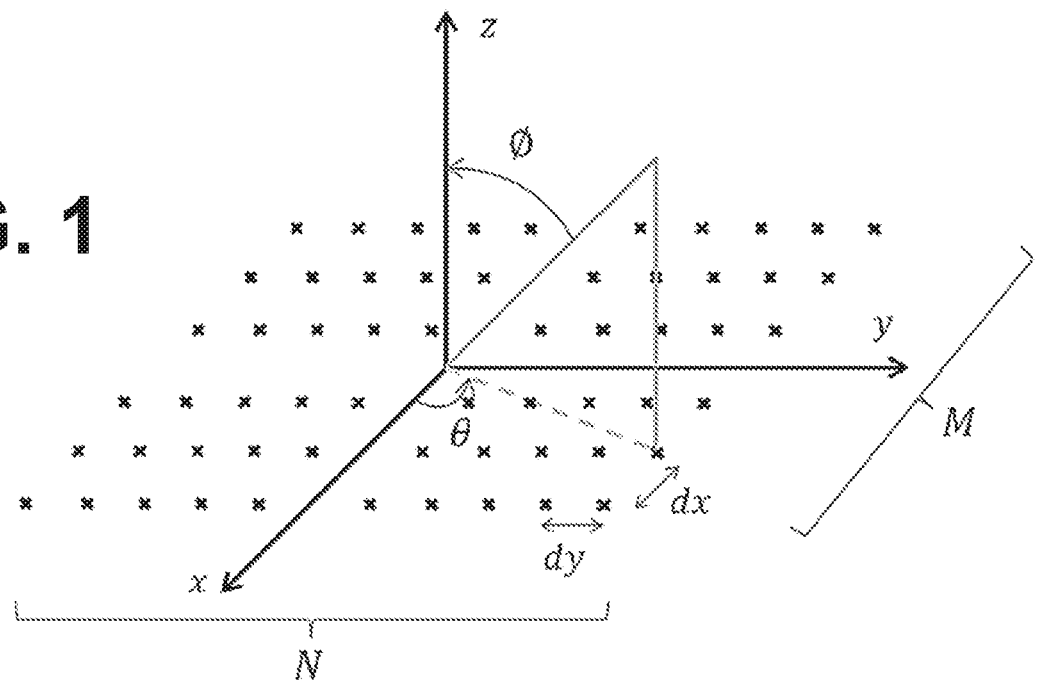
FIG. 1 illustrates an example of a linear planar array of M×N transmit antennas in accordance with various embodiments of the present disclosure.

Disclosed herein are various examples related to direct closed-form finite alphabet constant-envelope waveforms for planar array beampatterns. Reference will now be made in detail to the description of the embodiments as illustrated in the drawings, wherein like reference numbers indicate like parts throughout the several views.

In multiple-input multiple-output (MIMO) communication systems, multiple antennas are deployed at the transmitter and receiver to increase the data rate and provide multiple paths to mitigate the fading in the channel. Like MIMO communications, MIMO techniques can be applied to radar systems. MIMO radars offer extra degrees-of-freedom (DOF), which can be exploited for more diversity, higher spatial resolution, reduced side-lobe-levels at the receiver, and in order to design a variety of desired transmit beampatterns. Depending on how the antennas are distributed, MIMO radars can be classified into two categories: widely distributed and collocated. In widely distributed cases, the transmitting antennas are widely separated so that each antenna may view a different aspect of the target. This topology can increase the spatial diversity of the system. In contrast, the transmitting antennas in collocated systems are closely spaced to view the same aspect of the target. The collocated antennas do not provide spatial diversity, but can increase the spatial resolution of the radar system. Moreover, compared to phased-array radars, collocated radars can provide better control of the transmit beampattern.

In collocated MIMO radar systems, it is usually desirable to steer transmitted power in the region-of-interest. To do this, conventional methods optimize the waveform covariance matrix, R, for the desired beampattern, which is then used to generate actual transmitted waveforms. Both steps require constrained optimization. Most of the existing methods use iterative algorithms to solve these problems, therefore their computational complexity is very high that prevents them from being used in practice. In this disclosure, a closed-form solution is used to design the covariance matrix for a given beampattern using the planar array, which can then be used to derive a novel closed-form algorithm to directly design the finite-alphabet constant-envelope (FACE) waveforms without synthesizing the covariance matrix. The algorithm can exploit the two-dimensional discrete Fourier transform. Therefore, the computational complexity of the algorithm is very low and it can be used for large size antenna arrays to change the beampattern in real time. We also show, the number of snapshots needed to achieve desired beampattern depends on the beampattern and is less than the total number of transmit antennas. Due to the FACE property, the waveforms can be used to design multi-function software radar. The performance of the algorithm is compared with the existing iterative methods.

It is known that the transmit beampattern of a collocated antenna array radar depends on the cross-correlation between the transmitted waveforms from different antennas. To design correlated waveforms, for given transmit beampattern, early solutions have relied on a two-step process. In the first step, a user designs the waveform covariance matrix such that the theoretical transmitted power matches the desired beampattern as closely as possible. The second step then involves the design of the actual waveforms that can realize the designed covariance matrix. Both of these steps require constrained optimization and, in most of the available literature, iterative algorithms are used to solve these optimization problems. To synthesize the waveform covariance matrix for the given beampattern, efficient iterative algorithms have been proposed. These iterative algorithms are computationally very expensive for real-time applications.

A closed-form solution, to find the waveform covariance matrix, which is based on fast-Fourier-transform (FFT) has been proposed. Once the covariance matrix is synthesized, the corresponding waveforms fulfilling the practical constraints, such as constant-envelope (CE) or low peak-to-average power ratio (PAPR) are designed. To design such waveforms, an iterative algorithm was proposed. The main drawback of this algorithm is its high computational cost. Moreover, it can draw symbols from an infinite alphabet that can be challenging to use in practice. A closed-form solution can be used to generate finite-alphabet constant-envelope (FACE) waveforms to realize the given covariance matrix. In this algorithm, mapping of Gaussian random variables (RVs) onto binary phase-shift keying (BPSK) symbols is exploited and a cross-correlation relationship between the Gaussian and BPSK RVs is derived. The main drawback of this algorithm is that its performance is beampattern dependent. To tackle this problem, an iterative algorithm, which can be used to directly generate the best possible BPSK RVs (without synthesizing the covariance matrix) for the desired beampattern, was proposed by inverting the derived cross-correlation relationship between the Gaussian and BPSK RVs.

To match the desired beampatterns, the waveforms can also be designed directly without synthesizing the covariance matrix. However, optimal solutions to directly design the waveforms, fulfilling the constraints, for a given beampattern are not available. Using this approach, to directly design the waveforms for a uni-modal symmetric beampattern, a sub-optimal algorithm is presented. In this algorithm, a scalar coefficient is chosen to control the width of the beampattern. This method utilizes a high number of transmitting antennas in order to achieve good performance to match the desired beampattern.

Most of the solutions in the previous work deal only with a linear array and the region-of-interest (ROI) is defined by only one parameter, which is the azimuth angle. In planar array radar systems, the transmitting antennas form a plane and an additional dimension called the elevation angle is taken into account in order to provide a larger radar aperture. This allows for the characterization of the ROI in three-dimensional (3D) space. Various strategies for hybrid MIMO phased-array radar, based on multiplication of signal sets by a pseudo-noise spreading sequence, may be used for different transmit 3D beampatterns.

In this work, a closed-form solution is disclosed to design the waveform covariance matrix, for the desired 3D beampatterns, using a planar array radar. It is very expensive to synthesize waveform covariance matrix for large size planar array using semi-definite programming (SDP). Therefore, to reduce the computational complexity, the problem is mapped onto the two-dimensional (2D) fast Fourier transform (2D-FFT). By exploiting the derivations of the covariance matrix, a method to directly design the FACE waveforms, without synthesizing the covariance matrix for the desired beampattern, is presented. Since the waveforms are directly derived from the covariance matrix in closed-form, the beampattern of the closed-form covariance matrix and waveforms is exactly same. Benefits of the disclosed algorithm include:

- a closed-form solution is provided to design a covariance matrix and waveforms for the desired beampattern using planar array;
- synthesis of covariance matrix not needed for beampattern design;
- finite-alphabet constant-envelope (FACE) waveforms can be provided to design a software radar;
- a reduced number of snapshots (less than the number of total antenna elements in the array); and
- very low computational complexity.

This disclosure is organized as follows. Initially, the signal model adopted for the planar array is presented and the optimization problem formulated for the beampattern design. Next, by exploiting 2D-FFT, an algorithm to design covariance matrix for the desired beampattern is presented. The computational complexity to design covariance matrix using the algorithm and SDP method is then presented. The direct design of the waveforms is next discussed, followed by discussion of simulation results.

Notations: Small letters, bold small letters, and bold capital letters respectively designate scalars, vectors, and matrices. If A is a matrix, then $A^H$ and $A^T$ respectively denote the Hermitian transpose and the transpose of A. v(i) denotes the $i^{th}$ element of vector v. A(i,j) denotes the entry in the $i^{th}$ row and $j^{th}$ column of matrix A. The Kronecker product is denoted by $\otimes$. Modulo M operation on an integer i is denoted by $\langle i \rangle_M$ and $\lfloor i \rfloor M$ denotes the quotient of i over M. Finally, the statistical expectation is denoted by $E\{\cdot\}$.

System Model and Problem Formulation

Consider a MIMO radar system with a rectangular planar-array, composed of M×N omni-directional collocated antennas, placed at the origin of a unit radius sphere as shown in FIG. 1. The inter-element-spacing (IES) between any two adjacent antennas in the x-axis and y-axis directions can be represented by $d_x$ and $d_y$, respectively. If a spatial location around this planar-array has an azimuth angle θ and an elevation angle φ, the corresponding Cartesian coordinates of this location can be written as:

$$x = \sin(\phi)\cos(\theta) \text{ and } y = \sin(\phi)\sin(\theta)$$

Define the baseband transmitted signal vector containing the transmitted symbols from all antennas at time index n as:

$$x(n) = [x_{0,0}(n), \ldots, x_{0,N-1}(n), \ldots, x_{M-1,N-1}(n)]^T, \quad (1)$$

where $x_{p,q}(n)$ denotes the transmitted symbol from the antenna at the $(p, q)^{th}$ location at time index n. For narrow band signals with non-dispersive propagation, the signal received by a target located at location defined by the azimuth angle θ and the elevation angle φ can be written as:

$$r(n; \theta, \phi) = \sum_{p=0}^{M-1}\sum_{q=0}^{N-1} x_{p,q}(n) e^{j2\pi \frac{d_x(p,q)\sin(\phi)\cos(\theta)}{\lambda}} e^{j2\pi \frac{d_y(p,q)\sin(\phi)\sin(\theta)}{\lambda}}. \quad (2)$$

Assume that the distance between any two adjacent antennas along the x-axis and y-axis is λ/2, $d_x(p, q) = q\lambda/2$ and $d_y(p, q) = p\lambda/2$. This simplifies Eqn. (2) to:

$$r(n; \theta, \phi) = \sum_{p=0}^{M-1}\sum_{q=0}^{N-1} x_{p,q}(n) e^{j2\pi q \frac{\sin(\phi)\cos(\theta)}{2}} e^{j2\pi p \frac{\sin(\phi)\sin(\theta)}{2}}.$$

By exploiting the relationship between the spherical and Cartesian coordinates, given in Eqn. (1), the received signal can be written in terms of Cartesian coordinates as:

$$r(n; f_x, f_y) = \sum_{p=0}^{M-1}\sum_{q=0}^{N-1} x_{p,q}(n) e^{j2\pi(qf_x + pf_y)}, \quad (3)$$

where $$f_x = \frac{\sin(\phi)\cos(\theta)}{2} \text{ and } f_y = \frac{\sin(\phi)\sin(\theta)}{2} \quad (4)$$

are the normalized Cartesian coordinates of the same spatial location. It should be noted here that $-0.5 \leq \{f_x, f_y\} \leq +0.5$. The received signal in Eqn. (3) can be written in vector form as:

$$r(n; f_x, f_y) = a_s^H(f_x, f_y) x(n), \quad (5)$$

where $$a_s(f_x, f_y) = \begin{bmatrix} 1 \\ e^{j2\pi f_y} \\ \vdots \\ e^{j2\pi(M-1)f_y} \end{bmatrix} \otimes \begin{bmatrix} 1 \\ e^{j2\pi f_x} \\ \vdots \\ e^{j2\pi(N-1)f_x} \end{bmatrix}. \quad (6)$$

Using Eqn. (3), the received power at the location $(f_x, f_y)$ can be easily written as:

$$B(f_x, f_y) = E\{a_s^H(f_x, f_y) x(n) x(n)^H a_s(f_x, f_y)\} \quad (7)$$
$$= a_s^H(f_x, f_y) R a_s(f_x, f_y),$$

where $R = E\{x(n)x(n)H\}$ is the MN×MN covariance matrix of the transmitted waveforms. This yields a degree of freedom (DOF) of $$\frac{(MN)^2 + MN}{2}.$$

In the conventional transmit beampattern design problem, a covariance matrix, R, is synthesized to match the transmitted power B(φ, θ) to the desired beampattern which involves the minimization of the following cost function:

$$J(R) = \sum_{l=1}^{L}\sum_{k=1}^{K} |a_s^H(f_x(l), f_y(k))Ra_s(f_x(l), f_y(k)) - \alpha P_d(f_x(l), f_y(k))|_2^2, \quad (8)$$

where $P_d(f_x(l), f_y(k))$ is the desired beampattern defined over the two dimensional grid $(\{f_x(l)\}_{l=1}^L, \{f_y(k)\}_{k=1}^K)$ and $\alpha$ is a scaling factor. Since the matrix R is a covariance matrix, it should be positive semi-definite. Moreover, radio frequency power amplifiers (RFPA) have limited dynamic range and cannot transmit all power levels with the same power efficiency. To design a variety of transmit beampatterns without changing any hardware, the RFPA should transmit same power levels for any beampattern. Therefore, to satisfy these constraints using the conventional methods, the minimization problem in Eqn. (8) can be re-formulated as follows:

$$\begin{cases} \min J(R) \\ \text{subject to} \\ c_1: R \succeq 0 \\ C_2: R(n,n) = c, n = 1, 2, \ldots, MN. \end{cases} \quad (9)$$

$C_1$ represents the semi-definite constraint and $C_2$ ensures a uniform constant elemental power. The constrained problem in Eqn. (9) can be optimally solved using an iterative SDP method. However, for a large number of antennas, the computational complexity of the SDP method becomes prohibitively large. Therefore, such solutions may not be feasible for planar-arrays of higher sizes. In order to reduce the computational cost by exploiting 2D-FFT algorithm, a closed-form solution can be used to find the matrix R as discussed in the following section. The SDP algorithm is considered hereafter as a benchmark.

Proposed Covariance Matrix Design

For any M×N time domain matrix $H_t$, an M×N frequency domain matrix H can be generated. The relationship between the time domain coefficients $H_t(m, n)$ and the frequency domain coefficients $H_f(k_1, k_2)$ can be given by the following 2D discrete-Fourier-transform (2D-DFT) formula:

$$H_f(k_1, k_2) = \sum_{m=0}^{M-1}\sum_{n=0}^{N-1} H_t(m,n) e^{-j2\pi k_1 m/M} e^{-j2\pi k_2 n/N}. \quad (10)$$

Similarly, for given frequency domain coefficients, the time domain coefficients can be obtained with the 2D inverse discrete-Fourier-transform (2D-IDFT) as follows:

$$H_t(m, n) = \frac{1}{MN}\sum_{k_1=0}^{M-1}\sum_{k_2=0}^{N-1} H_f(k_1, k_2) e^{j2\pi k_1 m/M} e^{j2\pi k_2 n/N}. \quad (11)$$

Using Eqn. (10), the following lemma can be obtained:

Lemma 1: Let $H_f$ be an M×N matrix with real positive frequency domain coefficients and define the vectors $e_M(k_1)$ and $e_N(k_2)$ as:

$$e_M(k_1) = [1 \quad e^{j2\pi k_1/M} \quad \ldots \quad e^{j2\pi k_1(M-1)/M}]^T, \quad (12)$$

$$e_N(k_2) = [1 \quad e^{j2\pi k_2/N} \quad \ldots \quad e^{j2\pi k_2(N-1)/N}]^T,$$

where $k_1=0, 1, \ldots, M-1$ and $k_2=0, 1, \ldots, N-1$. If a matrix $R_{hh}$ is constructed as:

$$R_{hh} = \frac{1}{(MN)^2}\sum_{k_1=0}^{M-1}\sum_{k_2=0}^{N-1} H_f(k_1, k_2) e(k_1, k_2) e^H(k_1, k_2), \quad (13)$$

where $(k_1,k_2)=e_N(k_2)\otimes e_M(k_1)$, then $e_N(k_2)$ will be positive semi-definite and all of its diagonal elements will be equal. Moreover, the individual elements of $H_f$ are related to the entries of $R_{hh}$ using the following quadratic form:

$$H_f(l_1, l_2) = e^H(l_1, l_2) R_{hh} e(l_1, l_2). \quad (14)$$

A detailed proof of Lemma 1 is given in the Appendix below.

Finding $R_{hh}$ using Eqn. (13) can be computationally very expensive since it performs the outer product of MN vectors and the addition of MN matrices. To reduce the computational complexity, the individual elements of $R_{hh}$ can be written, using Eqn. (13), as:

$$R_{hh}(i_1, i_2) = \frac{1}{(MN)^2}\sum_{k_1=0}^{M-1}\sum_{k_2=0}^{N-1} H_f(k_1, k_2) \times e^{j\frac{2\pi k_1 (\langle i_1 - i_2\rangle_M)}{M}} e^{j\frac{2\pi k_2 (\lfloor i_1\rfloor_M - \lfloor i_2\rfloor_M)}{N}}, \quad (15)$$

where $i_1, i_2 = 0, 1, \ldots, MN-1$. Comparing Eqn. (15) with Eqn. (11), Eqn. (15) can be rewritten as:

$$R_{hh}(i_1, i_2) = \frac{1}{MN} h_t(\langle i_1 - i_2\rangle_M, \lfloor i_1\rfloor_M - \lfloor i_2\rfloor_M). \quad (16)$$

For a given frequency domain matrix $H_f$, the time domain matrix $H_t$ can be found using the FFT. Therefore, finding $R_{hh}$ using $H_t$ is computationally less expensive. It should also be noted here that since $H_f$ is real, $H_t(-m, -n) = H_t^*(m,n)$, moreover as $$e^{-j\frac{2\pi k_1 m}{M}} = e^{j\frac{2\pi k_1(M-m)}{M}}$$

the matrix $R_{hh}$ will be a block Toeplitz.

Note that a uniform linear array can be considered a planar array with N=1. In this case, the frequency and time domain matrices $H_f$ and $H_t$ are now reduced to M×1 vectors denoted respectively as $h_f$ and $h_t$. The correlation matrix $R_{hh}$ becomes of dimension M×M and, by using Eqn. (13), the individual elements of $R_{hh}$ can be found as:

$$R_{hh}(i_1, i_2) = \frac{1}{M^2}\sum_{k_1=0}^{M-1} h_f(k_1) e^{\frac{2j\pi k_1 \langle i_1 - i_2\rangle_M}{M}}, \quad (17)$$

$$= \frac{1}{M^2}\sum_{k_1=0}^{M-1} h_f(k_1) e^{\frac{2j\pi k_1 (i_1 - i_2)}{M}}.$$

Similarly, using the fact that h is real, the matrix $R_{hh}$ can be found using the time domain coefficients of $h_t$ as:

$$R_{hh}(i_1, i_2) = \frac{1}{M} h_t(i_1 - i_2). \quad (18)$$

Since $h_t(-i)=h_t^*(i)$, the matrix $R_{hh}$ is a Toeplitz matrix. Thus, the method for two dimensional beampatterns (defined by $\theta$ and $\phi$) is also valid for one dimensional beampatterns. In addition, a computationally efficient closed-form solution is provided below for the transmitted waveforms satisfying the desired beampattern.

Since the matrix $R_{hh}$ is positive semi-definite and all of its diagonal elements are equal, it satisfies both the $C_1$ and $C_2$ constraints of the optimization problem in Eqn. (9) for designing the desired beampattern.

Therefore, if $R_{hh}$ is considered to be the waveform covariance matrix, by comparing Eqn. (7) with Eqn. (14), it can be easily noticed that the problem of transmit beampattern design can be mapped to the result obtained in the Lemma 1. This transformation only requires the mapping of steering vector $a_s(f_x, f_y)$ to $e(k_1, k_2)$. This can be done by mapping the values of $f_x$ and $f_y$ to $k_1$ and $k_2$ using the following expressions:

$$\begin{cases} f_x \mapsto -0.5 + \frac{k_1}{M-1}, & k_1 = 0 \ldots M-1 \\ f_y \mapsto -0.5 + \frac{k_2}{N-1}, & k_2 = 0 \ldots N-1. \end{cases} \quad (19)$$

It should be noted that using this mapping, $f_x$ and $f_y$ define the desired beampattern and have discrete values. This can be a drawback for small sized planar antenna arrays due to the small spatial resolution. The desired beampattern will be defined in terms of $f_x$ and $f_y$, however the beampattern in terms of spherical coordinates can be found using Eqn. (4).

The two dimensional space can then be defined by a two dimensional grid $(\{f_x(l)\}_{l=1}^L, \{f_y(k)\}_{k=1}^K)$ represented by an M×N matrix $H_f$. Thus, the entry $H_f(m, n)$ corresponds to $$f_x = -0.5 + \frac{m}{M-1} \text{ and } f_y = -0.5 + \frac{n}{N-1}.$$

In order to define the ROI of the desired beampattern, assign "1" to the entries of $H_f$ that are inside the ROI and "0" everywhere else. The steps to compute R are summarized in TABLE 1.

TABLE 1

| | |
|---|---|
| Step 0: | Define $H_f$ according to the ROI |
| Step 1: | Determine $H_t \leftarrow$ 2D-IDFT($H_f$) |
| Step 2: | Compute $R_{hh}$ using Eqn. (16) |
| Step 3: | Use $R_{hh}$ as the waveform covariance matrix R |

Figure 2:
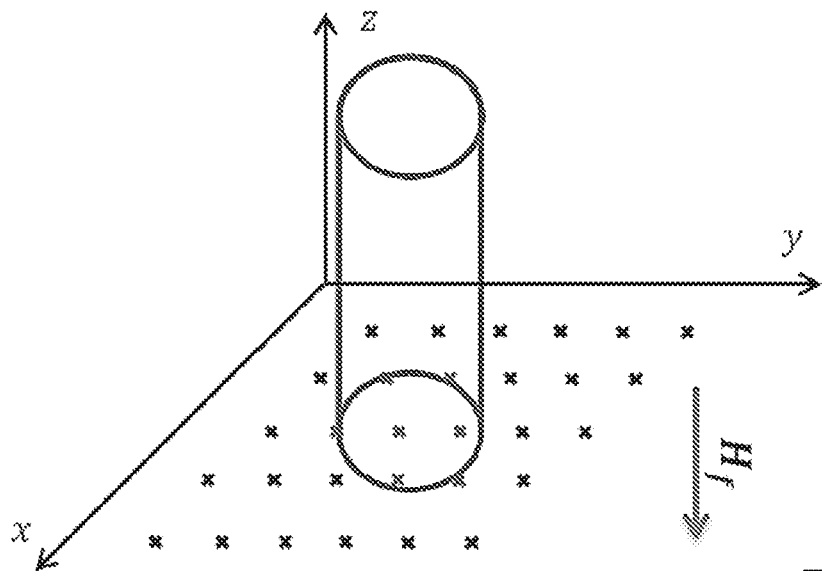
FIG. 2 illustrates an example of element selection of matrix $H_f$ associated with the linear planar array of FIG. 1 to produce a circular shaped beam pattern in accordance with various embodiments of the present disclosure.

It is worth noting that different forms of beampatterns can be obtained by changing the coefficients of the matrix $H_f$. For example, a circular shaped beam can be designed by filling $H_f$ with ones and zeros as shown in FIG. 2, and following the steps of TABLE 1 to obtain the corresponding waveform covariance matrix.

Computational Complexity

As it can be seen from TABLE 1, the only computational complexity of the method comes from the IDFT computation step. The NM IDFT coefficients are computed using one of the famous FFT algorithms which have a complexity equal to O(MN log(MN)) computations. However, the SDP method used in the previous discussion has a complexity of the order $O(\log(1/\eta)) (MN)^{3.5}$ for a given accuracy, $\eta$.

Once the covariance matrix is designed, waveforms to realize this covariance matrix are next designed. To design waveforms, most of the proposed algorithms are iterative and their computational complexity is high. In the following, the algorithm does not require the design of a waveforms covariance matrix, but rather it can directly design the waveforms in closed-form for the given desired beampattern. This further reduces the computational complexity of the beampattern design.

Direct Design of Waveforms for the Desired Beampattern

In this section, a closed-form expression to directly design the waveforms for the desired beampattern is described. Start from Eqn. (13), which can also be written as:

$$R(i_1, i_2) = \sum_{k_1=0}^{M-1} \sum_{k_2=0}^{N-1} \left( \frac{\sqrt{H_f(k_1, k_2)}}{MN} e^{j\frac{2\pi k_1 (i_1)_M}{M}} e^{j\frac{2\pi k_2 \lfloor i_1 \rfloor_M}{N}} \right) \times \quad (20)$$

$$\left( \frac{\sqrt{H_f(k_1, k_2)}}{MN} e^{j\frac{2\pi k_1 (i_2)_M}{M}} e^{j\frac{2\pi k_2 \lfloor i_2 \rfloor_M}{N}} \right)^*.$$

Assuming $k = k_1 + Mk_2 = \langle k \rangle_M + M\lfloor k \rfloor_M$, both terms in the above equation can be considered as the kth elements of the waveforms $s_{i_1}$ and $s_{i_2}$ that can be written as:

$$s_{i_1} k = \frac{\sqrt{H_f(\langle k \rangle_M, \lfloor k \rfloor_M)}}{MN} e^{j\frac{2\pi \langle k \rangle_M (i_1)_M}{M}} e^{j\frac{2\pi \lfloor k \rfloor_M \lfloor i_1 \rfloor_M}{N}},$$

$$s_{i_2} k = \frac{\sqrt{H_f(\langle k \rangle_M, \lfloor k \rfloor_M)}}{MN} e^{j\frac{2\pi \langle k \rangle_M (i_2)_M}{M}} e^{j\frac{2\pi \lfloor k \rfloor_M \lfloor i_2 \rfloor_M}{N}},$$

where $k=0, 1, \ldots, MN-1$ represents the time index. Thus, the cross-correlation between the waveforms $\{s_{i_1}(k)\}$ and $\{s_{i_2}(k)\}$ can be written as:

$$R(i_1, i_2) = \sum_{k=0}^{MN-1} s_{i_1}(k) s_{i_2}(k)^*. \quad (21)$$

The corresponding waveform vector can be written as:

$$s_i = \begin{bmatrix} \frac{\sqrt{H_f(0,0)}}{MN} e^{j\frac{2\pi(0)\langle i\rangle_M}{M}} e^{j\frac{2\pi(0)\lfloor i\rfloor_M}{N}} \\ \vdots \\ \frac{\sqrt{H_f(0,N-1)}}{MN} e^{j\frac{2\pi(0)\langle i\rangle_M}{M}} e^{j\frac{2\pi(N-1)\lfloor i\rfloor_M}{N}} \\ \vdots \\ \vdots \\ \frac{\sqrt{H_f(M-1,0)}}{MN} e^{j\frac{2\pi(M-1)\langle i\rangle_M}{M}} e^{j\frac{2\pi(0)\lfloor i\rfloor_M}{N}} \\ \vdots \\ \frac{\sqrt{H_f(M-1,N-1)}}{MN} e^{j\frac{2\pi(M-1)\langle i\rangle_M}{M}} e^{j\frac{2\pi(N-1)\lfloor i\rfloor_M}{N}} \end{bmatrix} = \begin{bmatrix} v_0^i \\ \vdots \\ v_{M-1}^i \end{bmatrix} \quad (22)$$

where $$v_p^i = \begin{bmatrix} \frac{1}{MN}\sqrt{H_f(p,0)}\, e^{j\frac{2\pi(0)\lfloor i\rfloor_M}{N}} e^{j\frac{2\pi p\langle i\rangle_M}{M}} \\ \frac{1}{MN}\sqrt{H_f(p,N-1)}\, e^{j\frac{2\pi(N-1)\lfloor i\rfloor_M}{N}} e^{j\frac{2\pi p\langle i\rangle_M}{M}} \end{bmatrix}, \quad (23)$$

while $p=0, 1, \ldots, M-1$. Therefore, for any transmitting element of the rectangular array at the (m, n)th location, where $m=0 \ldots M-1$ and $n=0 \ldots N-1$, assign the waveform $s_i$ defined in Eqn. (22) with $i=m+nM$. It should be noted here that, depending on the desired beampattern, some elements of the waveform $s_i$ may be equal to zero. If $N_a$ is the number of non-zero elements in the matrix $H_f$, the ith waveform will be transmitting only $N_a$ non-zero symbols. It should also be noted here that the time index of non-zero elements in each waveform will be the same. Therefore, for the desired beampattern only $N_a < MN$ snapshots will be needed.

Peak to Average Power Ratio (PAPR): the performance of the waveform design method was examined in terms of PAPR. For $N_a$ non-zero elements in the matrix $H_f$, the average transmitted power from the antenna at the (m, n)th location can be written as:

$$P_i(avg) = \frac{1}{N_a} s_i^H s_i,$$

$$= \frac{1}{N_a} \sum_{k=0}^{MN-1} \frac{1}{(MN)^2} s_i(k) s_i^*(k),$$

$$= \frac{N_a}{N_a(MN)^2}.$$

Note that the average transmitted power does not depend on the antenna location, which confirms that the uniform elemental power constraint is satisfied. Similarly, the peak power of the ith waveform can be derived as:

$$P_i(\text{peak}) = \max_k \left| \frac{\sqrt{H_f(\langle k\rangle_M, \lfloor k\rfloor_M)}}{MN} e^{j\frac{2\pi\langle k\rangle_M \langle i\rangle_M}{M}} e^{j\frac{2\pi\lfloor k\rfloor_M \langle i\rangle_M}{N}} \right|^2 \quad (24)$$

$$= \max_k \left| \frac{H_f(\langle k\rangle_M, \lfloor k\rfloor_M)}{(MN)^2} \right| = \frac{1}{(MN)^2}.$$

Therefore, the PAPR can be found as:

$$PAPR = \frac{P_i(\text{peak})}{P_i(avg)} = \frac{1/(MN)^2}{1/(MN)^2} = 1. \quad (25)$$

From Eqn. (25), it can be seen that the PAPR is equal to one for any antenna.

Numerical Simulations

Beampattern: the performance of the proposed FFT-based algorithm is investigated in this section. For simulation, a rectangular planar array composed of M×N antennas is considered. The spacing between any two adjacent antennas on the x-axis and y-axis of the planar-array is kept at $\lambda/2$. The mean squared-error (MSE) between the desired and designed beampatterns is defined as:

$$MSE = \sum_{l=1}^{L}\sum_{k=1}^{K} |a_s^H(f_x(l), f_y(k)) R a_s(f_x(l), f_y(k)) - \alpha P_d(f_x(l), f_y(k))|^2 / KL.$$

Figure 3:
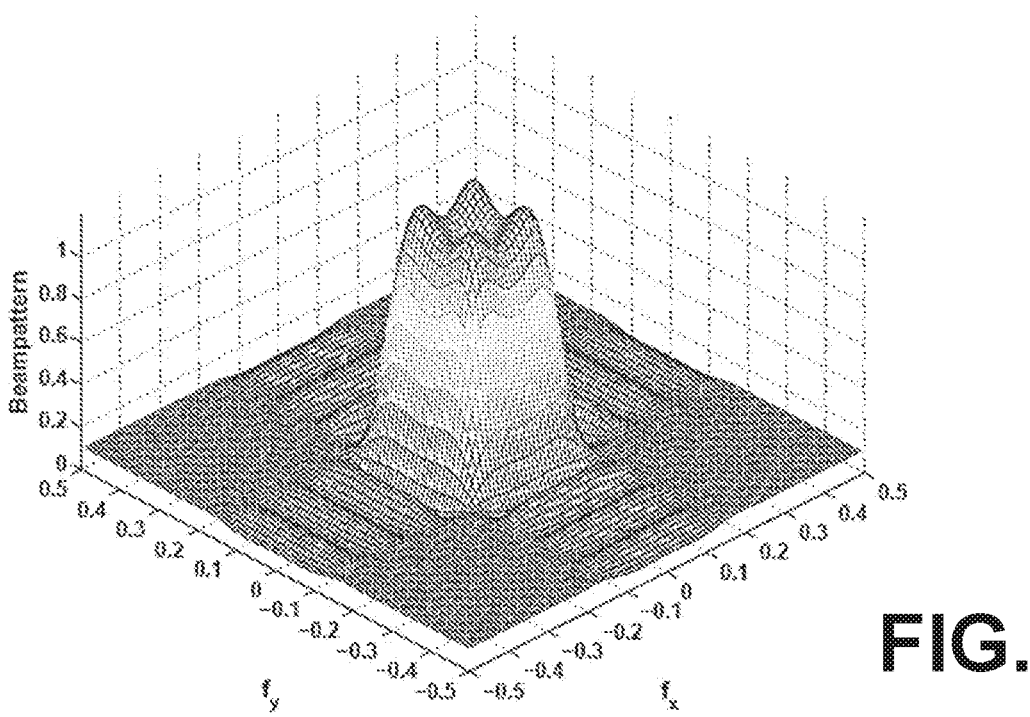
FIG. 3 illustrates an example of a beampattern realization using an iterative semi-definite programming (SDP) having a region-of-interest (ROI) defined by $-0.1 < f_x < 0.1$ and $-0.1 < f_y < 0.1$.

In the first simulation, the ROI was defined as $-0.1 \le f_x \le 0.1$ and $-0.1 \le f_y \le 0.1$, while the number of transmit and receive antennas was N=M=10. To design this beampattern, first R was synthesized using an SDP method. The designed beampattern using the synthesized covariance matrix based on the SDP method is shown in FIG. 3, which is the best possible designed beampattern in terms of a MSE sense. Note that the beampattern was normalized by dividing by $\alpha$. For this simulation, the total number of antennas was 100, therefore, to synthesize the covariance matrix, the simulation was very time consuming. Here, the actual waveforms to realize the synthesized covariance matrix were not designed as they also require high computational complexity iterative algorithm. The designed beampattern with the actual waveforms may be degraded too.

Figure 4:
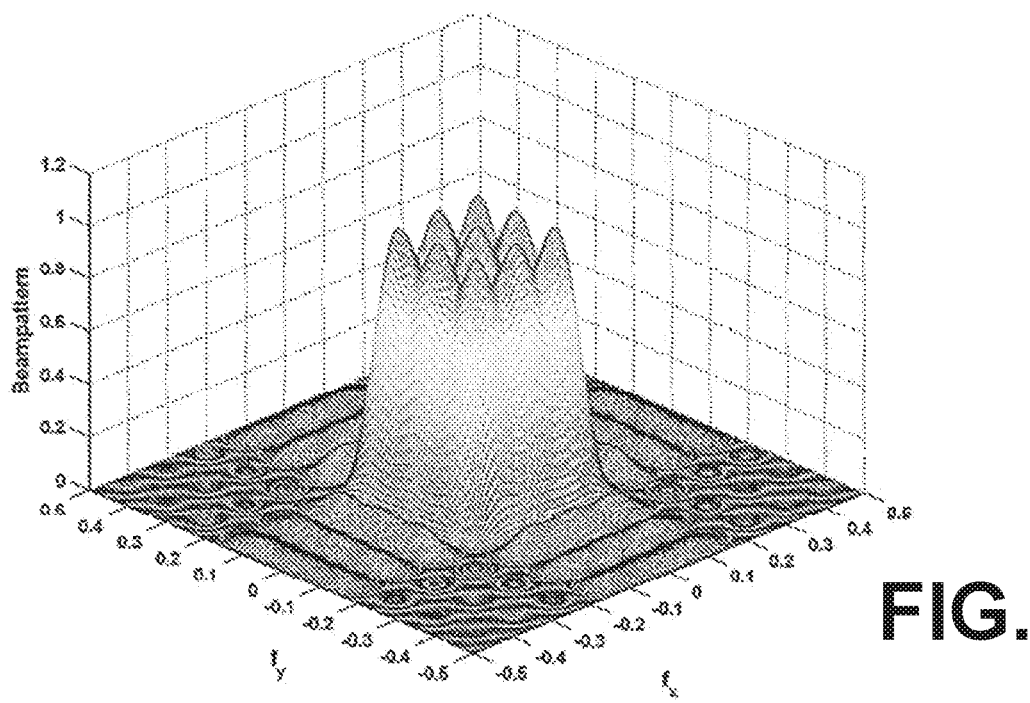
FIG. 4 illustrates an example of a beampattern realization using a proposed closed-form fast Fourier transform (FFT) based method having a ROI defined by $-0.1 < f_x < 0.1$ and $-0.1 < f_y < 0.1$ in accordance with various embodiments of the present disclosure.
Figure 5:
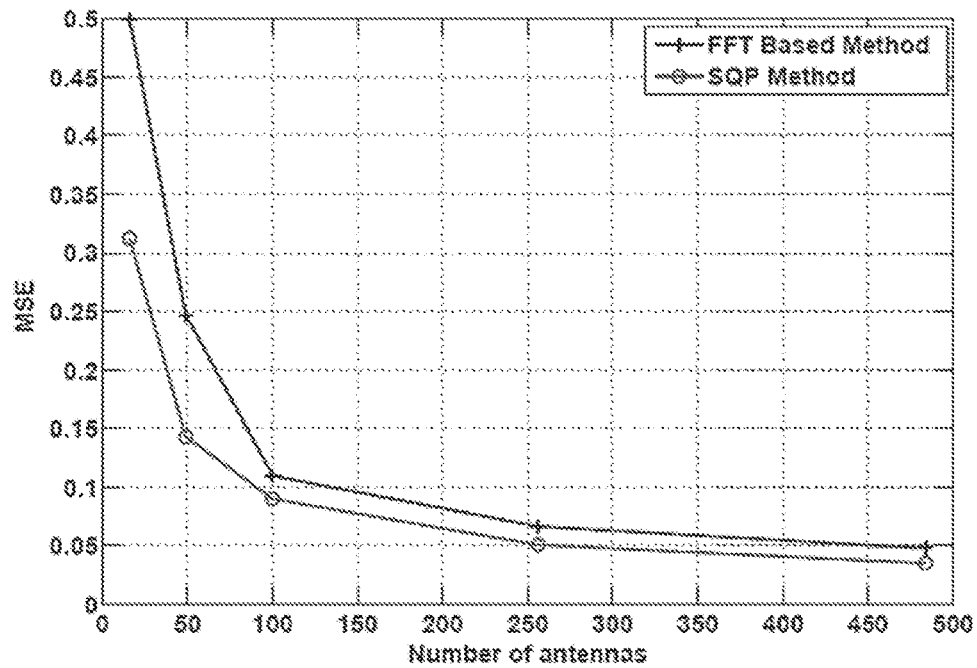
FIGS. 5 and 6 illustrate comparisons of the mean square error and complexity of the beampattern examples of FIGS. 3 and 4 in accordance with various embodiments of the present disclosure.

In order to reduce the computational complexity to synthesize the covariance matrix for the desired beampattern, the closed-form 2D-FFT based algorithm was used in the second simulation. The corresponding designed beampattern of the covariance matrix based on the 2D-FFT is shown in FIG. 4. The ROI was again defined as $-0.1 \le f_x \le 0.1$ and $-0.1 \le f_y \le 0.1$, and the number of antennas was N=M=10. In order to compare the performance of both algorithms, shown in the 2D-FFT and SDP based simulations for the beampatterns of FIGS. 3 and 4, the corresponding MSE for different planar array dimensions is shown in FIG. 5. Note that for a low number of antennas, the performance of the FFT-based method is affected. This may be attributed to the fact that the ROI (represented by the matrix $H_f$) is constructed in the two dimensional grid ($\{(f_{k1})_l\}_{l=1}^{M}, \{(f_{k2})_k\}_{k=1}^{N}$) whose resolution is related to the number of antennas. However, as the dimensions of the rectangular array increase, the method achieves a lower MSE level approaching the SDP-based method with the advantage of being much less complex.

Figure 6:
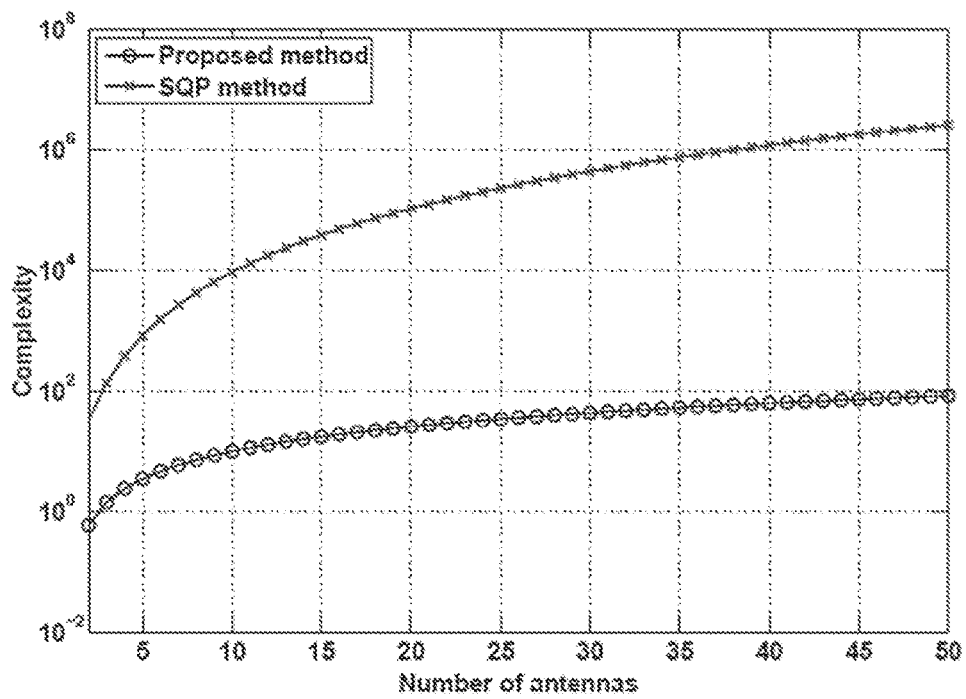
Figure 7:
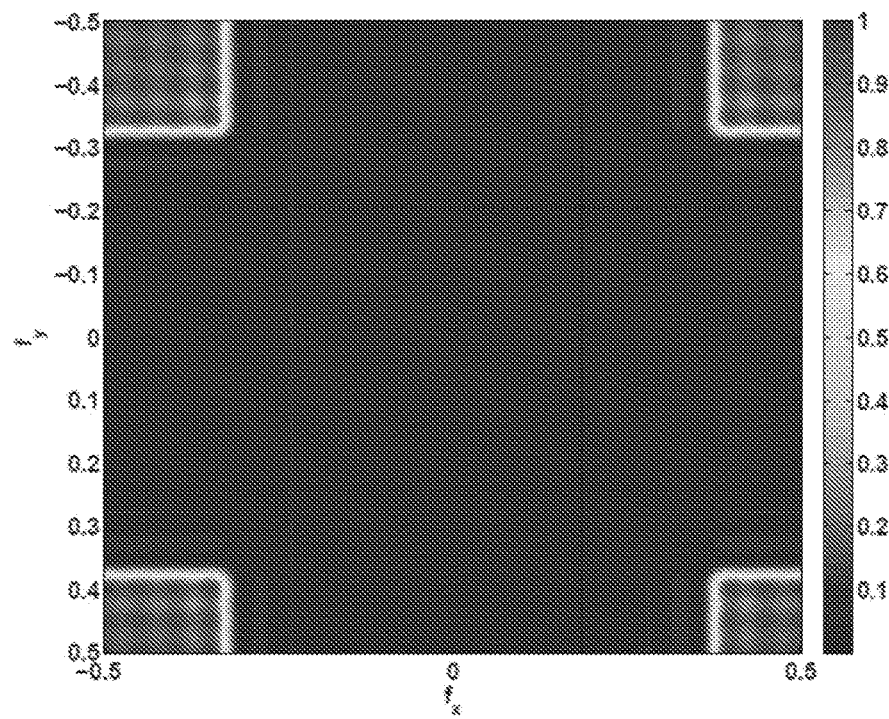
FIG. 7 illustrates an example of a beampattern realization focused on the corners using the proposed closed-form FFT based method in accordance with various embodiments of the present disclosure.

The computational complexity of both the SDP and 2D-FFT based algorithms with respect to the total number of elements in the planar array is shown in FIG. 6. It can be seen in the FIG. 6, the gap of computational complexity between the FFT-based and SDP-based algorithms increases with the number of antennas which makes the 2D-FFT based method more suitable for real-time radar applications. Next, by defining various desired beampatterns, corresponding covariance matrices were designed using the FFT-based algorithm described in TABLE 1. In this algorithm, depending on the desired beampattern, the corresponding locations in the matrix $H_f$ are mapped with ones or zeros. Note that in order to obtain good results, the symmetry of the beampattern should be respected.

Figure 8:
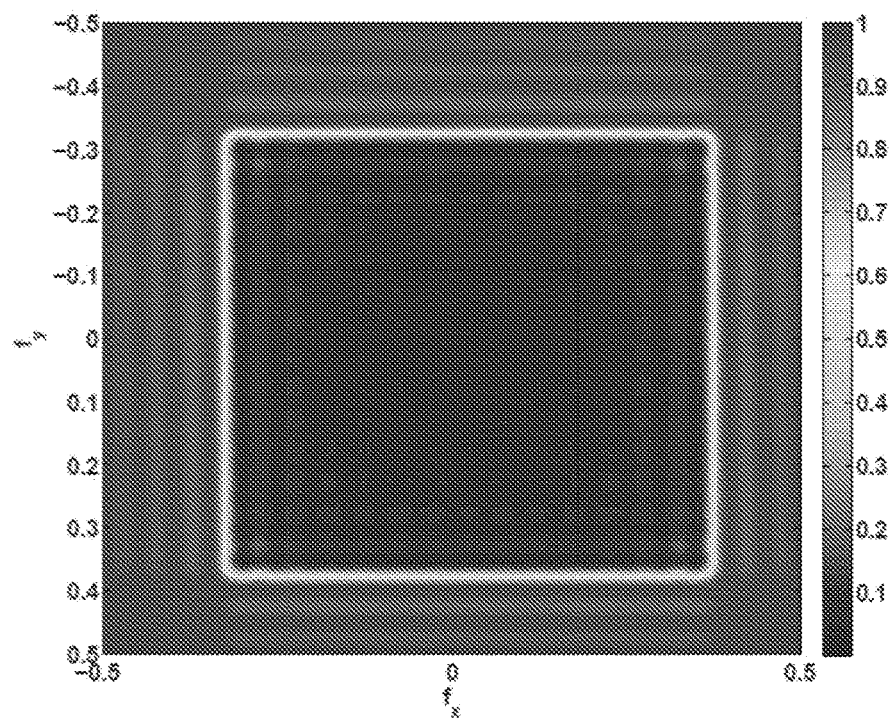
FIG. 8 illustrates an example of a beampattern realization focused on the borders using the proposed method in accordance with various embodiments of the present disclosure.
Figure 9:
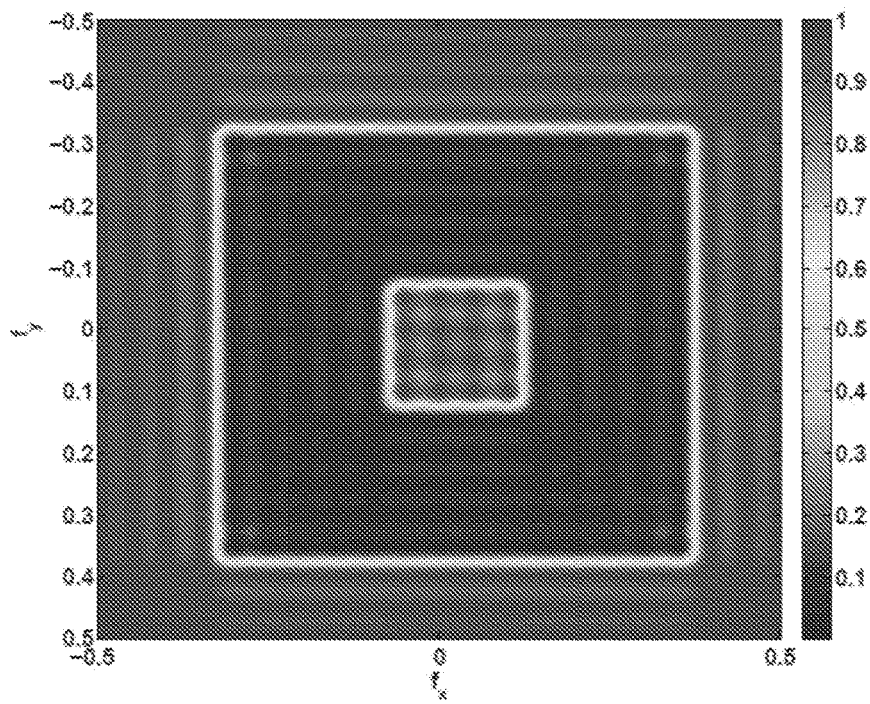
FIG. 9 illustrates an example of a beampattern realization focused on the corners and the borders using the proposed closed-form FFT based method in accordance with various embodiments of the present disclosure.
Figure 10:
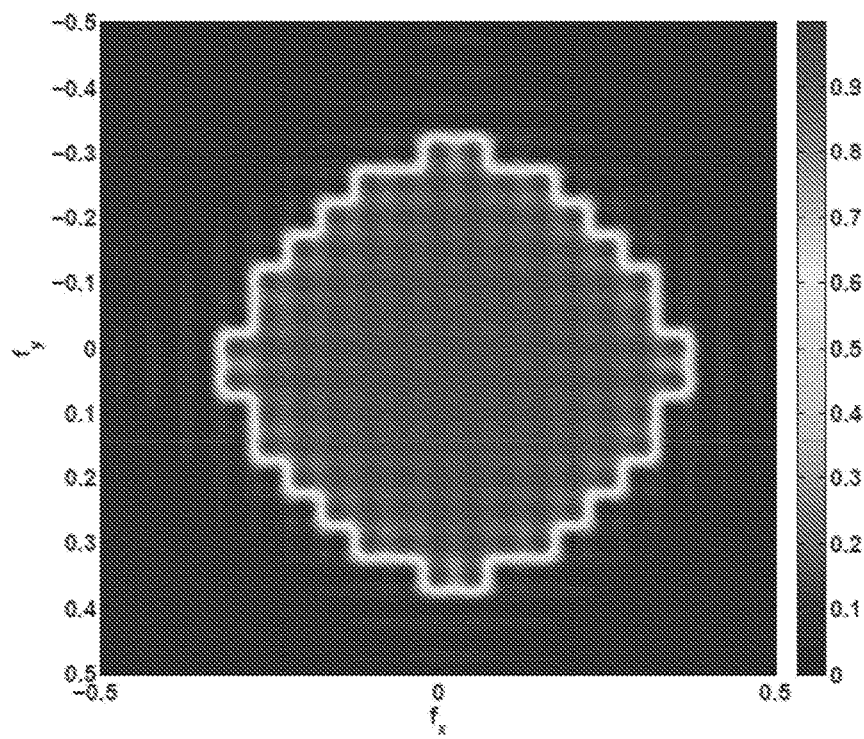
FIG. 10 illustrates an example of a circular beampattern realization using the proposed method in accordance with various embodiments of the present disclosure.
Figure 11:
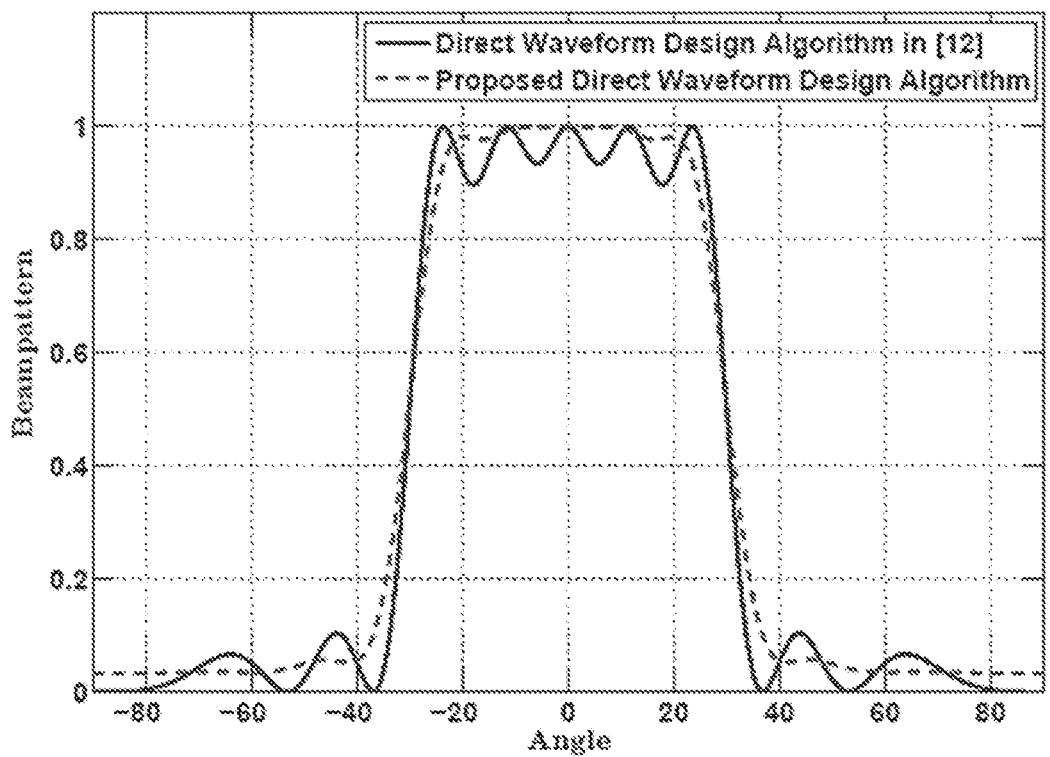
FIG. 11 illustrates a comparison of direct waveform design methods for a desired beam pattern using linear array in accordance with various embodiments of the present disclosure.

FIGS. 7-10 show various beampatterns that are designed using a planar array of dimensions N=M=20. In the FFT-based beampattern of FIG. 7, the transmitted power is focused only in the corners. In FIG. 8, the power is transmitted only on the borders. In FIG. 9, the transmitted power is focused both in the borders and center. Finally, FIG. 10 shows a circular shaped beampattern as illustrated in FIG. 2. As described above, the waveforms can be directly designed for the given beampattern without designing the covariance matrix. In the final simulation, a linear array of ten antennas was used. To transmit the power between the azimuth angle −30° and 30°, waveforms were directly designed using the 2D-FFT based algorithm and the algorithm proposed in "Signaling strategies for the hybrid MIMO phased-array radar" by Fuhrmann et al. (*IEEE Journal of Selected Topics in Signal Processing*, vol. 4, pp. 66-78, February 2010), which is hereby incorporated by reference in its entirety. The simulation results are shown in FIG. 11. It can be seen in FIG. 11 that the proposed algorithm yields almost uniform transmit power in the ROI, however, the designed beampattern has slower roll-off and higher side-lobe-levels compared to the 2D-FFT based algorithm. For this beampattern, the 2D-FFT based algorithm needs only five symbols for each waveform, while for the algorithm proposed by Fuhrmann et al., ten symbols are generated for each waveform.

Transmitter Implementation

Figure 12:
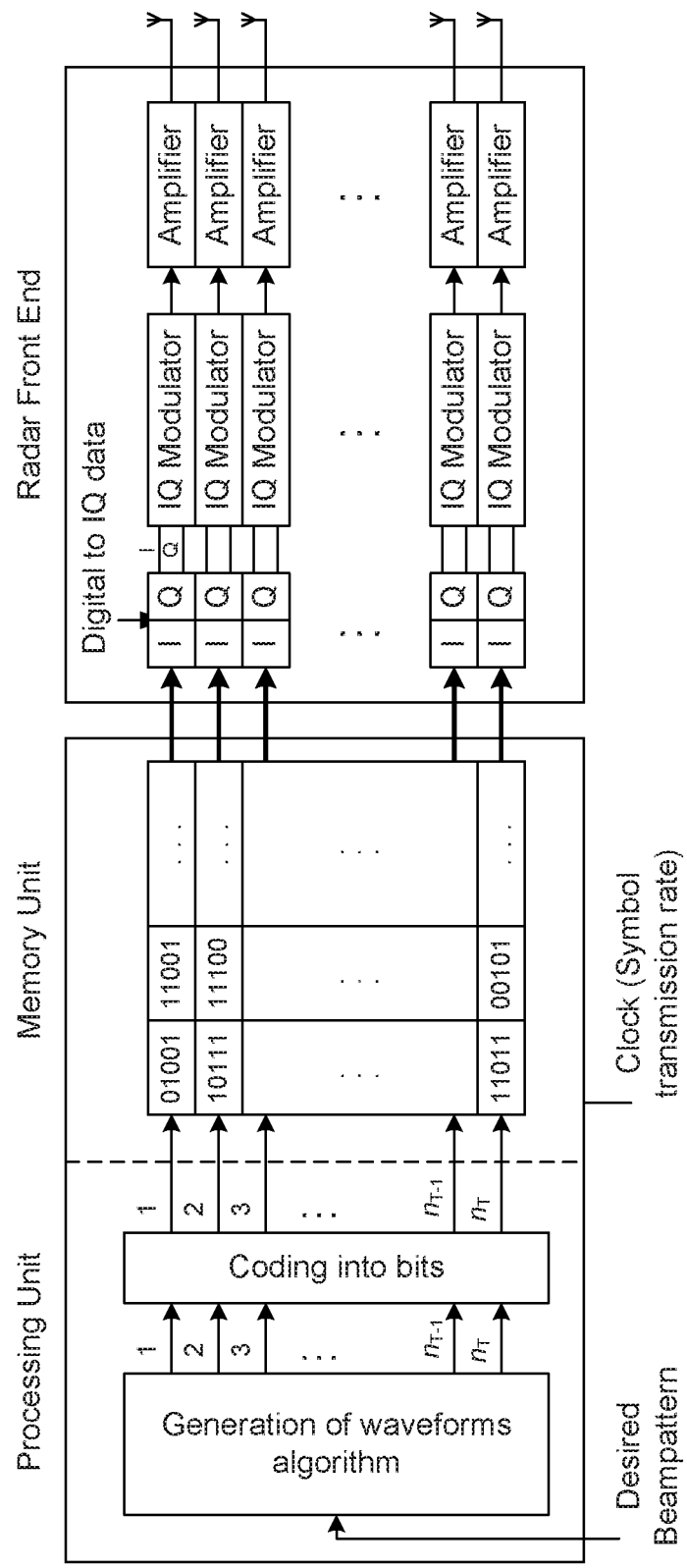
FIG. 12 is a schematic block diagram of an example of a radar system in accordance with various embodiments of the present disclosure.

The block diagram of the system is shown in FIG. 12. As can be seen in FIG. 12, a desired beampattern is input into the system, which will be a matrix of ones and zeros. The total number of elements in the matrix defines the grid points of the spatial locations. If the power is desired at some location, the corresponding element in the desired beampattern matrix is assigned one otherwise it is assigned zero. For the input beampattern, a waveform can be directly designed using the algorithms presented above. The real and imaginary parts of the symbols of the designed waveform can be coded into the corresponding digital bit streams. Each coded bit stream can be fed into the corresponding storage unit, where each bit stream is converted into analogue IQ data stream. Finally, the IQ data is modulated, amplified, and transmitted at the symbol transmission rate from the corresponding antenna. In this radar system, the beampattern can be changed adaptively.

Figure 13:
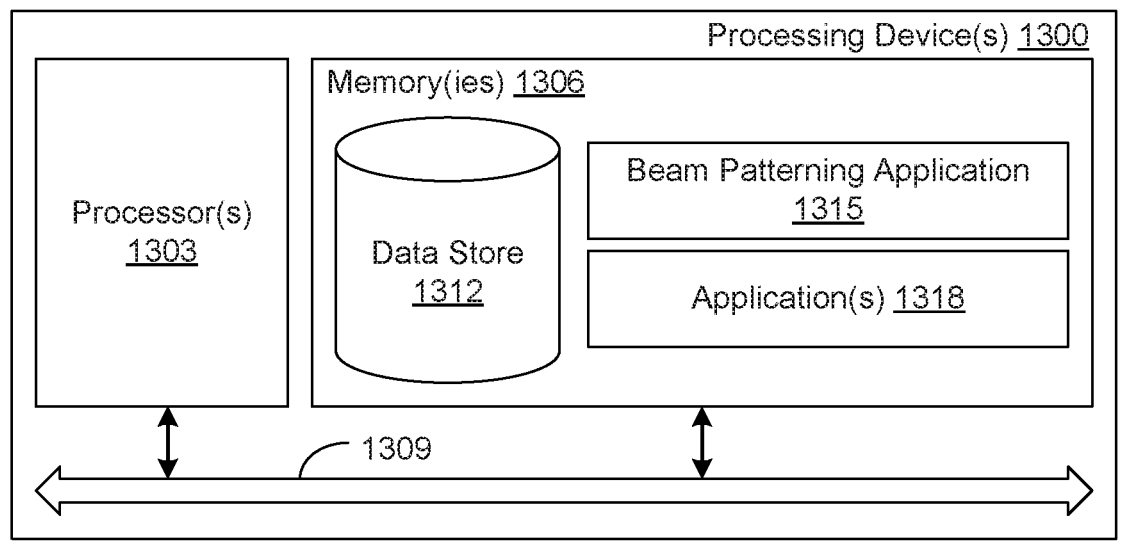
FIG. 13 is a schematic block diagram of a processing device in accordance with various embodiments of the present disclosure.

With reference to FIG. 13, shown is a schematic block diagram of a processing device 1300 according to various embodiments of the present disclosure. The processing device 1300 includes at least one processor circuit, for example, having a processor 1303 and a memory 1306, both of which are coupled to a local interface 1309. To this end, the processing device 1300 can comprise, for example, at least one computer or like device, which may be used to control radar transmissions. The local interface 1309 can comprise, for example, a data bus with an accompanying address/control bus or other bus structure as can be appreciated.

Stored in the memory 1306 are both data and several components that are executable by the processor 1303. In particular, stored in the memory 1306 and executable by the processor 1303 may be a beampatterning application 1315 and/or other applications 1318. Also stored in the memory 1306 can be a data store 1312 and other data. In addition, an operating system can be stored in the memory 1306 and executable by the processor 1303.

It is understood that there can be other applications that are stored in the memory 1306 and are executable by the processor 1303 as can be appreciated. Where any component discussed herein is implemented in the form of software, any one of a number of programming languages can be employed such as, for example, C, C++, C #, Objective C, Java®, JavaScript®, Perl, PHP, Visual Basic®, Python®, Ruby, Delphi®, Flash®, or other programming languages.

A number of software components are stored in the memory 1306 and are executable by the processor 1303. In this respect, the term "executable" means a program file that is in a form that can ultimately be run by the processor 1303. Examples of executable programs can be, for example, a compiled program that can be translated into machine code in a format that can be loaded into a random access portion of the memory 1306 and run by the processor 1303, source code that can be expressed in proper format such as object code that is capable of being loaded into a random access portion of the memory 1306 and executed by the processor 1303, or source code that can be interpreted by another executable program to generate instructions in a random access portion of the memory 1306 to be executed by the processor 1303, etc. An executable program can be stored in any portion or component of the memory 1306 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1306 is defined herein as including both volatile and nonvolatile memory and data storage components. Volatile components are those that do not retain data values upon loss of power. Nonvolatile components are those that retain data upon a loss of power. Thus, the memory 1306 can comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM can comprise, for example, static random access memory (SRAM), dynamic random access memory (DRAM), or magnetic random access memory (MRAM) and other such devices. The ROM can comprise, for example, a programmable read-only memory (PROM), an erasable programmable read-only memory (EPROM), an electrically erasable programmable read-only memory (EEPROM), or other like memory device.

Also, the processor 1303 can represent multiple processors 1303 and the memory 1306 can represent multiple memories 1306 that operate in parallel processing circuits, respectively. In such a case, the local interface 1309 can be an appropriate network that facilitates communication between any two of the multiple processors 1303, between any processor 1303 and any of the memories 1306, or between any two of the memories 1306, etc. The local interface 1309 can comprise additional systems designed to coordinate this communication, including, for example, performing load balancing. The processor 1303 can be of electrical or of some other available construction.

Although the beampatterning application 1315, application(s) 1318, and other various systems described herein can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the sequence of TABLE 1 shows a specific order of execution, it is understood that the order of execution may differ from that which is depicted. For example, the order of execution of two or more blocks may be scrambled relative to the order shown. Also, two or more steps shown in succession in TABLE 1 may be executed concurrently or with partial concurrence. Further, in some embodiments, one or more of the steps shown in TABLE 1 may be skipped or omitted (in favor, e.g., measured travel times). In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the patterning application 1315 and/or application(s) 1318, that comprises software or code can be embodied in any non-transitory computer-readable medium for use by or in connection with an instruction execution system such as, for example, a processor 1303 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium can be a random access memory (RAM) including, for example, static random access memory (SRAM) and dynamic random access memory (DRAM), or magnetic random access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

In this disclosure, a closed-form method of covariance matrix design and a direct closed-form solution of waveform design for the desired transmit beampattern using planar transmit antenna array is presented. The 2D-FFT algorithm exploits discrete Fourier transform to reduce the computational complexity and find the close-form solutions. For the covariance matrix design, the method fulfills both positive semi-definite and equal elemental power constraints. While for waveform design, the proposed method fulfills finite alphabet and constant envelope constraints. The numerical simulations presented confirm that the method is computationally efficient and performs closely to the SDP-based method as the number of antennas increases.

APPENDIX

The proof of Lemma 1 is straightforward. By exploiting the orthogonality of the vectors defined in Eqn. (12), $e^H(l_1, l_2)e(m_1, m_2) = MN\delta_{l_1 m_1}\delta_{l_2 m_2}$ where $\delta_{ij}$ in the Kronecker delta. Thus, we obtain:

$$e^H(l_1, l_2)R_{hh}e(l_1, l_2) = \frac{1}{(MN)^2}\sum_{k_1=0}^{M-1}\sum_{k_2=0}^{N-1}H_f(k_1, k_2)$$

$$e^H(l_1, l_2)e(k_1, k_2)e^H(k_1, k_2)e(l_1, l_2)$$

$$= \frac{1}{(MN)^2}\sum_{k_1=0}^{M-1}\sum_{k_2=0}^{N-1}H_f(k_1, k_2)$$

$$(MN)^2\delta_{l_1 k_1}\delta_{l_2 k_2}$$

$$= H_f(l_1, l_2).$$

Since $H_f(k_1, k_2) \geq 0$ for $k_1 = 0, 1, \ldots, M-1$ and $k_2 = 0, 1, \ldots, N-1$ and $R_{hh}$ is the sum of multiple rank 1 positive semi-definite matrices, $R_{hh}$ is positive semi-definite.

To prove that all the diagonal elements of $R_{hh}$ are equal, find the expression the ith diagonal element $R_{hh}(i, i)$ from the formula in Eqn. (13):

$$R_{hh}(i, i) = \frac{1}{(MN)^2}\sum_{k_1=0}^{M-1}\sum_{k_2=0}^{N-1}H_f(k_1, k_2)[e(k_1, k_2)e^H(k_1, k_2)](i, i).$$

Since $[e(k_1, k_2)e^H(k_1, k_2)](i, i) = 1$ for any index value i, the following can written:

$$R_{hh}(i, i) = \frac{1}{(MN)^2}\sum_{k_1=0}^{M-1}\sum_{k_2=0}^{N-1}H_f(k_1, k_2)$$

$$= \frac{N_a}{(MN)^2},$$

where $N_a$ is the number of non-zero elements in the frequency domain matrix $H_f$.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method, comprising:
defining, with processing circuitry, a waveform covariance matrix based at least in part upon a two-dimensional fast Fourier transform (2D-FFT) analysis of a frequency domain matrix $H_f$ associated with a planar array of antennas;
encoding symbols based upon the waveform covariance matrix; and
transmitting the encoded symbols via the planar array of antennas,
wherein individual elements of the waveform covariance matrix are determined from elements $H_t$ of a time domain matrix $H_t$, which is generated by a two-dimensional inverse discrete Fourier transform (2D-IDFT) of the frequency domain matrix $H_f$.

2. The method of claim 1, wherein the frequency domain matrix $H_f$ is based at least in part upon a defined region of interest (ROI) associated with the planar array of antennas.

3. The method of claim 2, wherein the individual elements of the frequency domain matrix $H_f$ correspond to individual antennas of the planar array of antennas, where individual elements corresponding to individual antennas within the ROI are assigned a value of one and individual elements corresponding to individual antennas outside the ROI are assigned a value of zero.

4. The method of claim 1, wherein the individual elements R of the waveform covariance matrix are determined from the elements $H_t$ of the time domain matrix $H_t$ based upon $$R(i_1, i_2) = \frac{1}{MN} H_t(\langle i_1 - i_2 \rangle_M, \lfloor i_1 \rfloor_M - \lfloor i_2 \rfloor_M)$$

where $i_1, i_2 = 0, 1, \ldots, MN-1$.

5. The method of claim 1, wherein the waveform covariance matrix is block Toeplitz.

6. The method of claim 1, wherein the transmitted encoded symbols are radar transmissions.

7. A system, comprising:
an N×M planar array of antennas, with N>2 and M>2; and
transmission circuitry configured to
define a waveform covariance matrix based at least in part upon a two-dimensional fast Fourier transform (2D-FFT) analysis of a frequency domain matrix $H_f$ associated with a planar array of antennas;
encode symbols based upon the waveform covariance matrix; and
transmit the encoded symbols via the planar array of antennas,
wherein individual elements of the waveform covariance matrix are determined from elements $H_t$ of a time domain matrix $H_t$, which is generated by a two-dimensional inverse discrete Fourier transform (2D-IDFT) of the frequency domain matrix $H_f$.

8. The system of claim 7, wherein the transmission circuitry comprises a processing unit configured to define the waveform covariance matrix and encode the symbols.

9. The system of claim 7, wherein the transmission circuitry comprises:
a memory unit configured to store a plurality of digital bit streams corresponding to the encoded symbols; and
a front end unit configured to transmit the plurality of digital bit streams corresponding to the encoded symbols through the planar array of antennas.

10. The system of claim 9, wherein the front end unit is a radar front end unit configured to transmit the encoded symbols through a planar array of radar antennas.

11. The system of claim 8, wherein the frequency domain matrix $H_f$ is based at least in part upon a defined region of interest (ROI) associated with the planar array of antennas.

12. The system of claim 8, wherein the individual elements of the frequency domain matrix $H_f$ correspond to individual antennas of the planar array of antennas, where individual elements corresponding to individual antennas within the ROI are assigned a value of one and individual elements corresponding to individual antennas outside the ROI are assigned a value of zero.

13. The system of claim 7, wherein the symbols are radar transmissions.

14. The system of claim 7, wherein the individual elements R of the waveform covariance matrix are determined from the elements $H_t$ of the time domain matrix $H_t$ based upon $$R(i_1, i_2) = \frac{1}{MN} H_t(\langle i_1 - i_2 \rangle_M, \lfloor i_1 \rfloor_M - \lfloor i_2 \rfloor_M)$$

where $i_1, i_2 = 0, 1, \ldots, MN-1$.

15. The system of claim 11, wherein the processing unit is configured to determine the frequency domain matrix $H_f$.

16. A method, comprising:
defining a region of interest (ROI) for a planar array of antennas;
defining a frequency domain matrix $H_f$ based on the defined region of interest;
determining a time domain matrix $H_t$ based on a two-dimensional fast Fourier transform (2D-FFT) analysis of the frequency domain matrix $H_f$;
determining a waveform covariance matrix based on the time domain matrix $H_t$;
encoding symbols based upon the waveform covariance matrix; and
transmitting the encoded symbols via the planar array of antennas.

17. The method of claim 16, wherein the planar array of antennas is an N×M planar array of antennas and the time domain matrix $H_t$ is determined based on $$H_t(m, n) = \frac{1}{MN} \sum_{k_1=0}^{M-1} \sum_{k_2=0}^{N-1} H_f(k_1, k_2) e^{j2\pi k_1 m/M} e^{j2\pi k_2 n/M}$$

wherein $H_t(m,n)$ are time domain coefficients and $H_f(k_1, k_2)$ are frequency domain coefficients.

18. The method of claim 16, wherein the transmitted encoded symbols are radar transmissions.

* * * * *